(12) United States Patent
Stromberg et al.

(10) Patent No.: US 12,171,793 B2
(45) Date of Patent: Dec. 24, 2024

(54) METHOD OF ACTIVATING LACTIC ACID BACTERIA

(71) Applicant: INFANT BACTERIAL THERAPEUTICS AB, Stockholm (SE)

(72) Inventors: Staffan Stromberg, Nacka (SE); Eamonn Connolly, Lindingo (SE); Stefan Roos, Uppsala (SE)

(73) Assignee: INFANT BACTERIAL THERAPEUTICS AB, Stockholm (SE)

( * ) Notice: Subject to any disclaimer, the term of this patent is extended or adjusted under 35 U.S.C. 154(b) by 423 days.

(21) Appl. No.: 15/320,996

(22) PCT Filed: Jan. 14, 2016

(86) PCT No.: PCT/EP2016/050694
§ 371 (c)(1),
(2) Date: Dec. 21, 2016

(87) PCT Pub. No.: WO2016/113363
PCT Pub. Date: Jul. 21, 2016

(65) Prior Publication Data
US 2017/0304376 A1    Oct. 26, 2017

Related U.S. Application Data

(60) Provisional application No. 62/103,201, filed on Jan. 14, 2015.

(51) Int. Cl.
| | |
|---|---|
| A61K 35/747 | (2015.01) |
| A23L 33/135 | (2016.01) |
| A61K 9/00 | (2006.01) |
| A61K 9/10 | (2006.01) |
| A61K 9/16 | (2006.01) |
| A61K 9/19 | (2006.01) |
| A61K 31/194 | (2006.01) |
| A61K 35/744 | (2015.01) |
| A61K 47/12 | (2006.01) |
| C12N 1/20 | (2006.01) |

(52) U.S. Cl.
CPC .......... *A61K 35/747* (2013.01); *A23L 33/135* (2016.08); *A61K 9/0053* (2013.01); *A61K 9/0095* (2013.01); *A61K 9/10* (2013.01); *A61K 9/1617* (2013.01); *A61K 9/1623* (2013.01); *A61K 9/19* (2013.01); *A61K 31/194* (2013.01); *A61K 35/744* (2013.01); *A61K 47/12* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 6,506,413 B1 * | 1/2003 | Ramaekers | A61K 31/19 424/529 |
| 2003/0017192 A1 | 1/2003 | Kanafani et al. | |
| 2007/0010003 A1 | 1/2007 | Berger | |
| 2009/0304656 A1 * | 12/2009 | Roos | A61P 17/00 424/93.45 |
| 2012/0171166 A1 | 7/2012 | Chow et al. | |
| 2013/0302297 A1 | 11/2013 | Gueniche | |

FOREIGN PATENT DOCUMENTS

| | | |
|---|---|---|
| CN | 104206539 | 12/2014 |
| JP | H07255467 | 10/1995 |
| JP | 2014234551 | 12/2014 |

OTHER PUBLICATIONS

Saulnier et al., PLoS One 6(4): e18783., pp. 1-14, 2011.*
Branen et al., Applied Microbiology, Jun. 1971, p. 993-998, vol. 21, No. 6.*
Dai et al., CN 104206539, 2014, machine translation.*
Kang, T.S. et al. 2013. Influence of oxygen on NADH recycling and oxidative stress resistance systems in Lactobacillus panis PM1. AMB Express 3(10): 1-9. specif. pp. 1, 2.*
Deman, J.C. et al. 1960. A medium for the cultivation of lactobacilli. Journal of Applied Bacteriology 23(1): 130-135. specif. pp. 131, 132, 134.*
Hunter, C. et al. 2012. Effect of routine probiotic, Lactobacillus reuteri DSM 17938, use on rates of necrotizing enterocolitis in neonates with birthweight <1000 grams: a sequential analysis. BMC Pediatrics 12(142): 1-6. specif. pp. 1, 2.*
Saulnier, D.M. et al. 2011. Exploring metabolic pathway reconstruction and genome-wide expression profiling in Lactobacillus reuteri to define functional probiotic features. PLoS One 6(4): 1-14. specif. pp. 1, 2, 3, 8.*
Branen, A.L. et al. 1970. Growth stimulation of Lactobacillus casei by sodium citrate. Journal of Dairy Science 53(5): 593-597. specif. pp. 593, 594, 595.*
Mortera, P. et al. 2013. Ca2+-citrate uptake and metabolism in Lactobacillus casei ATCC 334. Applied and Environmental Microbiology 79(15): 4603-4612. specif. pp. 4606, 4608.*
Hugenholtz, J. 1993. Citrate metabolism in lactic acid bacteria. FEMS Microbiology Reviews 12: 165-178; specif. pp. 165, 170, 171.*

(Continued)

*Primary Examiner* — Adam Weidner
*Assistant Examiner* — Sharon M. Papciak
(74) *Attorney, Agent, or Firm* — Myers Bigel, P.A.

(57) ABSTRACT

The present invention relates to methods of activating live lactic acid bacteria comprising exposing said bacteria to a preparation comprising citrate, wherein said bacteria have the ability to utilize citrate as an external electron acceptor. The present invention further relates to methods to enhance the activity of certain live bacteria in mammals. More specifically the invention relates to improve the wake-up of certain lactic acid bacteria from the freeze-dried state. The present invention also relates to preparations comprising said activated bacteria and therapeutic uses of said activated bacteria.

19 Claims, 3 Drawing Sheets

Specification includes a Sequence Listing.

(56) References Cited

OTHER PUBLICATIONS

De Man et al., "A medium for the cultivation of lactobacilli", Jan. 1, 1960, pp. 130-135, retrieved from the Internet: http://onlinelibrary.wiley.com/store/10.1111/j.1365-2672.1960.tb00188.x/asset/j.1365-2672.1960.tb00188.x.pdf?v=1&t=hc1ob2qr&s=b1241c80942d799923ab73acd28970e77f1cde9f; Abstract.

Abrams SA et al. Greater mortality and morbidity in extremely preterm infants fed a diet containing cow milk protein products. Breastfeeding Medicine. 2014; 9(6): 281-285.

Hickey MW et al. Metabolism of pyruvate and citrate in Lactobacilli. Aust. J. Blol. Sci. 1983; 36: 487-96.

Hunter CJ et al. Understanding the susceptibility of the premature infant to necrotizing enterocolitis (NEC). Pediatric Research. 2008; 63(2): 117-123.

Patel BK and JS. Necrotizing enterocolitis in very low birth weight Infants: a systemic review. ISRN Gastroenterology. vol. 2012, Article ID 562594, 7 pages.

Qin et al "A Proposed Genus Boundary for the Prokaryotes Based on Genomic Insights" Journal of Bacteriology, 196(12):2210-2215 (2014).

International Preliminary Report on Patentability, Written Opinion, and International Search Report corresponding to International Patent Application No. PCTEP16050694, dated Jul. 18, 2017, 23 pages.

Claesson et al. "The genus *Lactobacillus*—a genomic basis for understanding its diversity" FEMS Microbiology Letters, 269:22-28 (2007).

Saulnier et al. "Exploring Metabolic Pathway Reconstruction and Genome-Wide Expression Profiling in Lactobacillus reuteri to Define Functional Probiotic Features" PLoS One, 6(4):e18783 (2011).

Zheng et al. "A taxonomic note on the genus *Lactobacillus*: Description of 23 novel genera, emended description of the genus *Lactobacillus* Beijerinck 1901, and union of Lactobacillus and Leuconostocaceae" Int. J. Syst. Evol. Microbiol 70:2782-2858 (2020).

\* cited by examiner

METHOD OF ACTIVATING LACTIC ACID BACTERIA

STATEMENT OF PRIORITY

This application is a 35 U.S.C. § 371 national phase application of International Application Serial No. PCT/EP2016/050694, filed Jan. 14, 2016, which claims the benefit, under 35 U.S.C. § 119 (a) of U.S. Provisional Patent Application No. 62/103,201, filed Jan. 14, 2015, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 9737-49_ST25.txt, 798 bytes in size, generated on Aug. 20, 2024, and filed herewith, is hereby incorporated by reference in its entirety for its disclosures.

FIELD OF THE INVENTION

The present invention relates generally to enhancing the onset of activity of certain live bacteria in mammals. Moreover this invention relates to preparations comprising substrate components and certain live bacteria, the substrate components being specifically designed or selected to improve reconstitution and early growth of said bacteria.

BACKGROUND OF THE INVENTION

The effectiveness of live bacteria therapeutics is purpose and strain-specific, and different strains may contribute to the host health through different mechanisms. Different live bacteria can prevent or inhibit the proliferation of pathogens, suppress production of virulence factors by pathogens, modulate the immune response in a pro-inflammatory or an anti-inflammatory way and influence the host in a number of other ways.

*Lactobacillus reuteri* is a heterofermentative lactic acid bacterium and is frequently found in the gastrointestinal tract of humans and other animals. *L. reuteri* is considered an indigenous organism of the human gastrointestinal tract and is for example present on the mucosa of the gastric corpus, gastric antrum, duodenum, and ileum. Different *L. reuteri* strains have the ability to colonize the intestine, act as a diarrhea therapeutic agent, modulate the gut motility, function as an inhibitor of bacterial pathogens, immunologically modulate the gastrointestinal mucosa, function as an anti-inflammatory agent in the stomach etc.

A problem with oral administration of live bacteria is insufficient amounts and/or activity of the live bacteria in locations of the intestinal tract where they will assert their effects. This may have as a consequence that the dosage of live bacteria has to be increased and/or more frequent administration is needed and might also result in loss of activity. This leads to unnecessary costs, undesirable frequency of intake and/or decreased or non-existing health benefits.

In some specific applications of live bacteria it is most important to quickly after administration have active and metabolizing live bacteria for the wanted health effects, and in some of those applications the amounts of nutrients in the individual may have to be deliberately restricted for medical reasons. So the problem to solve is to quickly activate the selected live bacteria to be administered to an individual but with minimum of influence on nutrients given to the individual. The invention herein is intended to solve this problem for certain bacteria.

SUMMARY OF THE INVENTION

A primary object of the present invention is to provide an enhanced onset of activity of certain live bacteria in humans, especially in neonates. The enhanced onset of activity is based on improved (e.g. quicker or more rapid) reconstitution and early growth (e.g. improved growth or growth rate) of the live bacteria when administered to said neonate without significantly altering the nutrient content given to the neonate. Neonates include preterm-born infants to term-born infants.

In the invention herein, for a fast activation of the live bacteria in for example the premature infant, a new combination of substrate components to add to the product has been developed. The inventors surprisingly found that the addition of salts of citrate, preferably in combination with a carbon source, such as lactose, to the formulation mix, improved the reconstitution and early growth of *L. reuteri* DSM 17938 and similar bacteria. Strains that can use citrate as an electron acceptor in their metabolism, with minimum influence on the nutrient content given to the baby, should preferably be used in the invention herein.

More specifically, the object of the present invention is to provide preparations comprising substrate components, including citrate and certain live bacteria, the substrate components being specifically designed to improve reconstitution, wake-up and early growth of said live bacteria.

The present invention is based on the surprising finding that the presence of citrate (exposure to citrate) at the timepoint when certain bacteria are activated (i.e. when they transition from a dormant form to an active and metabolizing form) improves their activation, for example in terms of improved reconstitution, wake up and/or growth. In other words, the presence of citrate (exposure to citrate) provides a "kick-start" to the bacteria when they are activated.

Thus, the present invention provides a method of activating live bacteria, in particular lactic acid bacteria, comprising exposing said bacteria to a preparation comprising citrate, wherein said bacteria have the ability to utilize citrate as an external electron acceptor. In particular, said utilization of citrate results in an improved growth rate. Thus, the present invention also provides a method of activating live bacteria, in particular lactic acid bacteria, comprising exposing said bacteria to a preparation comprising citrate, wherein said bacteria have the ability to utilize citrate for improved growth rate.

In addition, the present invention provides a preparation comprising activated bacteria, in particular lactic acid bacteria, prepared, obtained or obtainable by the methods of the invention.

Thus, the present invention also provides a preparation comprising:
 (i) a live bacteria, in particular a lactic acid bacteria, which has the ability to utilize citrate as an external electron acceptor; and
 (ii) citrate.

In preferred embodiments, the bacteria in said preparation are dormant bacteria, for example the bacteria and the preparation is frozen, lyophilized or freeze-dried.

In a yet further aspect the invention provides the therapeutic uses of such citrate activated bacteria of the invention or preparations of the invention as described herein.

Thus, the present invention provides activated bacteria, in particular lactic acid bacteria, prepared, obtained or obtainable by the methods of the invention, for use in therapy, for example in the treatment of a subject with a condition which will benefit from administration of a faster activated live bacteria or a bacteria with an improved growth rate. Thus, in some embodiments of the invention, the steps of the activation method are performed, after which the activated bacteria are used in therapy.

The invention further provides a preparation comprising (i) a live bacteria, in particular lactic acid bacteria, which has the ability to utilize citrate as an external electron acceptor, and (ii) citrate, for use in therapy, for example in the treatment of a subject with a condition which will benefit from administration of a faster activated live bacteria or a bacteria with an improved growth rate.

Viewed alternatively, the present invention provides a citrate activated live bacteria, in particular lactic acid bacteria, for use in therapy, for example in the treatment of a subject with a condition which will benefit from administration of a faster activated live bacteria or a bacteria with an improved growth rate.

In a further aspect, the invention also provides the use of activated bacteria, in particular lactic acid bacteria, prepared, obtained or obtainable by the methods of the invention in the manufacture of a medicament or composition for the treatment of a subject with a condition which will benefit from administration of a faster activated live bacteria or a bacteria with an improved growth rate.

The invention further provides the use of a preparation comprising (i) a live bacteria, in particular lactic acid bacteria, which has the ability to utilize citrate as an external electron acceptor, and (ii) citrate, in the manufacture of a medicament or composition for the treatment of a subject with a condition which will benefit from administration of a faster activated live bacteria or a bacteria with an improved growth rate.

Viewed alternatively, the present invention provides the use of a citrate activated live bacteria, in particular lactic acid bacteria, in the manufacture of a medicament or composition for the treatment of a subject with a condition which will benefit from administration of a faster activated live bacteria or a bacteria with an improved growth rate.

Further aspects of the invention provide a method of treatment of a subject with a condition which will benefit from administration of a faster activated live bacteria or a bacteria with an improved growth rate, said method comprising administration of an effective amount of activated bacteria, in particular lactic acid bacteria, prepared, obtained or obtainable by the methods of the invention to said subject.

The invention further provides a method of treatment of a subject with a condition which will benefit from administration of a faster activated live bacteria or a bacteria with an improved growth rate, said method comprising administration of an effective amount of a preparation comprising (i) a live bacteria, in particular lactic acid bacteria, which has the ability to utilize citrate as an external electron acceptor, and (ii) citrate, to said subject.

Viewed alternatively, the present invention provides a method of treatment of a subject with a condition which will benefit from administration of a faster activated live bacteria or a bacteria with an improved growth rate, said method comprising administration of an effective amount of a citrate activated live bacteria, in particular lactic acid bacteria, to said patient.

The administration of the bacteria or bacterial preparations in said methods of treatment and uses of the invention is carried out in pharmaceutically or physiologically effective amounts, to subjects (mammals) in need of treatment. Thus, said methods and uses may involve the additional step of identifying a subject in need of treatment. Alternative and preferred embodiments and features of the invention as described elsewhere herein apply equally to these methods of treatment and uses of the invention.

DETAILED DESCRIPTION OF THE INVENTION AND PREFERRED EMBODIMENTS THEREOF

Figure 1:
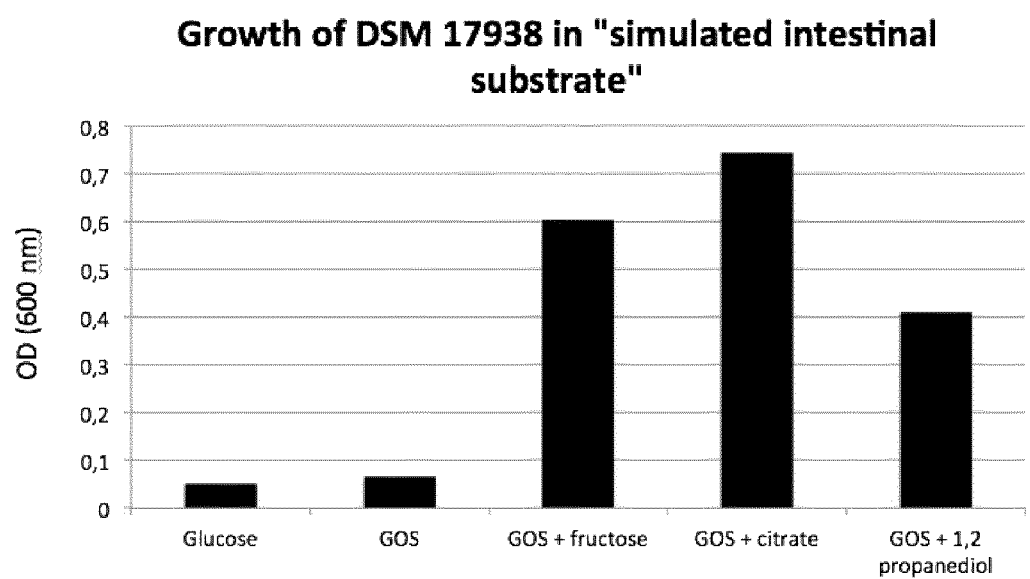
FIG. 1 is a graph that shows the growth of *Lactobacillus reuteri* DSM 17938 in "simulated intestinal substrate". Two different sources of carbohydrates were tested in combination with three different electron acceptors. The bacteria did not grow much only with carbohydrates but when electron acceptors were added, growth increased. Citrate as electron acceptor showed the highest effect.

To facilitate understanding of the invention, a number of terms are defined below.

"Neonatal", or "neonate" and "newborn" are used interchangeably and refer to a newborn child and the time period directly after birth. This term includes pre-term born infants or premature infants to term-born infants, and the time period directly after birth.

"Infant" and "baby" are used interchangeably and refer to a newborn baby and its first year of life (up to one year or up to twelve months old).

"Preterm" and "premature" refers to a birth that takes place before week 37 of pregnancy (or the equivalent timepoint in non-human mammals).

"Infection" refers to the invasion of a disease-causing microorganism.

A "metabolizing bacteria" is viable, meaning it grows and replicates utilizing suitable substrate components for example resulting in the production of metabolites and meaning that the bacteria can be used for specific purposes. "Dead bacteria" means a non-metabolizing bacteria that does not replicate and cannot be made viable.

"Dormant bacteria", means a non-metabolizing bacteria that does not replicate but is live and can be activated (or re-activated) to a metabolizing bacteria. Examples of such dormant bacteria are frozen or freeze-dried or lyophilised (or otherwise dried, e.g. spray-dried) bacteria. In turn a "dormant preparation" means a preparation comprising dormant bacteria, for example a frozen or freeze-dried or lyophilised (or otherwise dried, e.g. spray-dried) preparation.

"Live bacteria" means metabolizing bacteria or dormant bacteria that can be activated to metabolize.

"Activation" of bacteria means the process of changing the state of a bacterium from being dormant to the state of metabolizing bacteria.

The invention herein can be used to provide an enhanced onset of activity of certain live bacteria, especially when there are limited amounts of nutrients for the bacteria in the locality of administration. This is all done without significantly altering other nutritional status of the host.

In the present invention the local amounts and/or metabolic activity of for example selected *L. reuteri* are enhanced leading to, among other things, that the potential of lowering the dosage of the live bacteria and further that site-directed health benefits are possible.

NEC (necrotizing enterocolitis) is a medical condition primarily seen in premature infants. It is characterized by variable damage to the intestinal tract, ranging from mucosal injury to full-thickness necrosis and perforation where portions of the bowel undergo necrosis due to infection and inflammation in the intestine. It occurs postnatally and is the second most common cause of mortality in premature infants. Initial symptoms include feeding intolerance, increased gastric residuals, abdominal distension and bloody stools. For this unpredictable and devastating disease there is no definitive treatment. Thus, NEC prevention strategies are vital and urgently needed but to date none have been successful or generally adopted as the standard of care, and prophylaxis for NEC remains a true unmet medical need. The involvement of an abnormal gastrointestinal microbiota in NEC includes findings of bacteremia and endotoxemia in NEC infants and radiologic findings of pneumatosis intestinalis, which likely represents submucosal gas produced by bacterial fermentation.

It has been shown that preterm infants at the risk of receiving or developing NEC, or having NEC, benefit from *L. reuteri* DSM 17938 in their intestine to counteract the massive infection and inflammation associated with NEC. This procedure potentially saves lives in the NICU's (neonatal intensive care unit). The product is to be given to the baby via a nasogastric or orogastric (NG/OG) tube directly into the stomach.

In the first days of life of a preterm baby at risk of developing NEC, the provision of nutrients to keep the baby alive are normally given through parenteral delivery, and there are normally no nutrients initially given to the intestine. The reason for this is that early nutrients given through enteral feeding may induce NEC so nutrition is therefore given parenterally. This in turn means that there are no nutrients in the intestine to support the activation and growth of the needed lactic acid bacteria, particularly in the critical first days of life and particularly in premature infants. Since the intestine is a living environment there may be some limited nutrients and sugars available, but not to the extent to support a fast activation and early growth of the bacteria under those conditions.

The invention herein is to provide an improved solution to the problem by enabling a fast and selective activation of the live lactic acid bacteria or any other suitable live bacteria already when it is being delivered into the baby's intestine, for example, on route in the tube-feeding delivery system, with minimum influence on the nutrients given to the baby.

Normally human milk is the primary source of nutrition for newborn healthy babies. During the first days of lactation the mother produces what's called colostrum, which is a thin yellowish fluid rich in proteins and antibodies to provide the baby with a good start. After a few days the fluid will gradually change and become mature milk that contains protein, fat, carbohydrates and minerals. Carbohydrates mainly consist of lactose. At the first day of lactation the concentrations of citrate and lactose are normally as the following example: citrate 0.25 mM and lactose 76 mM, whereas on the fifth day of lactation the concentrations are as follows: citrate 5 mM and lactose 173 mM. Recalculated, this gives a ratio between citrate and lactose of 1:30 to 1:300.

For various reasons breast-feeding of a newborn baby may not be feasible, for example but not limited to preterm birth, complicated delivery, functional problems (e.g. the mother is not producing any or insufficient milk, blockage of milk ducts, mastitis), mother's illness etc. In such cases the baby needs nutrition in other ways and normally infant formulas are available and can be fed to the infants to compensate for lactation. In critical events, for example preterm infants where the infants have not had the time to develop properly in the uterus and often show an undeveloped bowel, it is central to quickly establish an environment in the intestine that would slow down an ongoing infection and inflammation. Preterm born babies are sensitive and need special care to be able to adapt to a life outside the uterus.

For neonates diagnosed or at risk of developing NEC, the product of the invention herein, is often given via a orogastric or nasogastric (OG/NG) tube directly into the stomach and nutrients to keep the baby alive are normally given through parenteral delivery, meaning that there are normally no nutrients initially given to the intestine.

In the invention herein, for a fast activation of the live bacteria in for example the premature infant, a new combination of substrate components to add to the preparation has been developed. The inventors surprisingly found that the addition of salts of citrate, preferably in combination with a carbon source, such as lactose, to the formulation mix improved reconstitution and early growth of *L. reuteri* DSM 17938.

By this invention, citrate acts as an external electron acceptor and releases the NAD (P) H brake in the metabolism by the specific bacteria.

In this regard, fermentation is a process that releases energy from a sugar and doesn't require oxygen or an electron transport chain. Instead an organic molecule is used as electron acceptor, carrying out the reoxidation of NAD (P) H produced during the glycolysis. Most often this organic molecule is pyruvate, the end product of the Embden-Meyerhof pathway (EMP), the most common type of glycolysis.

Homofermentative lactobacilli convert carbohydrates into lactate using the EMP, whereas heterofermentative lactobacilli (such as *L. reuteri*) use the phosphoketolase pathway (PKP). The PKP has a poor energy yield compared to that of the EMP, but this can be compensated for by the addition of external electron acceptors, which create alternative pathways for NAD (P) H reoxidation. This results in gaining one additional ATP, making the PKP as efficient as the EMP. In the present invention, citrate is used as an external electron acceptor and thus bacteria which have the ability to utilize citrate as an external electron acceptor are selected.

The carbon source, such as lactose, is specifically effective for fast growth of the strains adapted to human breast-milk and that are able to use citrate as an electron acceptor, such as *L. reuteri* DSM 17938.

The effect seen by *L. reuteri* DSM 17938 and citrate is strain-specific and for example other *Lactobacillus reuteri* strains such as *L. reuteri* ATCC PTA-4659, *L. reuteri* ATCC PTA-6475 and *L. reuteri* ATCC PTA-5289 are not able to use citrate as an electron acceptor and are thus not appropriate for use in the present invention. Citrate and lactose are present in human milk and are one of the basis for growth of *L. reuteri* DSM 17938 in milk.

The invention herein relates to the addition of citrate in proper ratio with lactose, or another suitable carbon source (for example other sugars such as sucrose, fructose, glucose or galacto-oligosaccharides (GOS)), in a product to be given to an individual who needs a rapidly activated live bacteria, such as *L. reuteri* DSM 17938 with minimum influence on the nutrients given. This will make the reconstitution and growth of *L. reuteri* DSM 17938 more like those conditions seen in the breast-fed infant gut in the first days of life.

The present invention aims to solve the health-related issues associated with the conditions of for example NEC by providing certain live and anti-inflammatory lactic acid bacterial strains such as *L. reuteri* DSM 17938, or strains with similar ability to utilize citrate as an electron acceptor, with an improved reconstitution and early growth capacity. The product of the invention could also be used for neonates that have difficulties in oral feeding and receive intravenous nutrition without being specifically diagnosed with NEC. The invention can further be used in other cases where a rapid activation of specific lactic acid bacteria would be beneficial from a health perspective.

The invention embodies a rapid activation of the lyophilized live bacteria in for example the premature infant by a new combination of substrate components to add to the final product. The invention further embodies the use of substrate components that are selected and mixed in a ratio that specifically would serve to support the enhanced onset of activity of the specific bacteria.

The present invention thus provides a method of activating live bacteria or improving activation of live bacteria by the addition or incorporation of citrate or otherwise exposing said bacteria to citrate (and optionally other substrate components). Activation of bacteria as described herein can take the form of improved reconstitution of a live bacterial preparation (e.g. when a dried, or otherwise dormant, and/or concentrated formulation of dormant bacteria is diluted and activated for use) which can in turn manifest itself as improved and/or more rapid growth of the live bacteria once the reconstitution has taken place, or the enhanced (increased) or faster onset of other bacterial activities, e.g. metabolism or colonization.

Thus, the activation methods of the invention, and the presence of citrate (exposure to citrate) in the formulations (e.g. in the final formulations for administration to the subject), give rise to the improved activation, e.g. the improved or more rapid reconstitution and/or improved or more rapid growth or growth rate of live bacteria, when compared to bacterial formulations which do not have citrate or an appropriate amount (i.e. an activating amount) of citrate in the formulation. Such use of citrate in formulations to activate live bacteria from a dormant state (e.g. when such bacteria are frozen, lyophilized, freeze-dried or otherwise dried) has, to the inventors' knowledge, not been disclosed before and results in an improved process for handling such bacteria, especially for certain medical treatments as described elsewhere herein.

For example, rapid activation of dormant live bacteria after (or before or during) administration of bacteria is important in some subjects, e.g. because subjects do not generally have nutrients in their stomach or intestine which can be used to efficiently activate dormant live bacteria, or because subjects may have amounts of nutrients deliberately restricted for medical reasons (e.g. infants having or at risk of having NEC). It may also be important to administer a composition which has the minimum of influence on nutrients given to the individual (e.g. in subjects where nutrients are deliberately restricted) or to administer a composition without significantly altering other nutritional status of the subject. In the formulations, methods and uses of the invention, there is sufficient nutrition in the formulation for the bacteria to get started (e.g. at least start to activate and grow) so that the bacteria does not have to scavenge for any limited nutrients that may be present in the intestine of the subject, e.g. the premature baby. This can be important as the amounts and content of the nutrition given to for example a baby suffering from or at risk of NEC have to be carefully regulated and balanced.

Hence, in such subjects, the bacteria need to be activated quickly without relying on existing nutrients in the intestine of the subject so that the therapeutic benefit is achieved as fast as possible and before the health of the host deteriorates. Fast activation after (or before or during) administration is also important because there is a lack of natural nutrients in the stomach of the host which will enable activation to take place within the subject.

The methods of the invention provide a solution to this problem by providing a method of activating live bacteria using citrate as a suitable substrate component for the bacteria and preferably also providing an appropriate carbon source for the bacteria such as a sugar (e.g. lactose).

Alternatively, the methods of activation as described herein can be viewed as the provision of a method of changing the state of a bacteria from being dormant to the state of metabolizing (e.g. the state of growing and replicating and preferably producing metabolites). The methods of activation as described herein can also be viewed as methods for reconstitution or growth of bacteria, for example methods of improving reconstitution and/or growth or growth rate of dormant live bacteria.

Advantageously, such improved activation of bacteria in accordance with the present invention can also result in a reduction of the required doses of bacteria, or result in less frequent administration of bacteria, or result in improved activity of the bacteria once administered (and hence therapeutic and health benefits).

Different strains and types of bacteria have different abilities. Appropriate live bacteria or microorganisms for use in the present invention are those which have the ability to utilize citrate as an external electron acceptor. The term "external electron acceptor" in the context of bacterial growth and metabolism is a term of the art. By "external" is for example meant that the electron acceptor (citrate) is derived from a source exogenous to the bacteria and is not derived from or produced by the bacteria itself.

Appropriate bacteria may also have the ability to use (or consume) citrate as a nutrient or substrate for growth (have the ability to grow in the presence of citrate), or to use citrate as an external electron acceptor in their metabolism (have the ability to metabolize citrate) or to have the ability to use citrate in a fermentation reaction (be citrate fermenting).

Preferred live bacteria are fermentative bacteria such as lactic acid bacteria, for example *Lactobacillus* or *Bifidobacterium*. Particularly preferred live bacteria are heterofermentative lactobacilli, e.g. which use the phosphoketolase pathway (PKP) to convert carbohydrates, such as *Lactobacillus reuteri*, in particular the strain *Lactobacillus reuteri* DSM 17938 or those with similar ability to utilize citrate as an external electron acceptor. The *Lactobacillus reuteri* DSM 17938 strain was deposited at the DSMZ-Deutsche Sammlung von Mikroorganismen und Zellkulturen GmbH (Mascheroder Weg 1b, D-38124 Braunschweig) on 30 Jan. 2006. In some embodiments of the invention, the *Lactobacillus reuteri* DSM 17938 strain is not used.

Preferred live bacteria for use in the present invention will also be capable of having a health benefit on the host or subject to which they are administered in adequate amounts. Thus, any live microorganism which would be useful for treating diseases or conditions or have any health benefit in a subject, in particular an infant or neonate, can be used in the present invention. For example, as described elsewhere herein, as the methods of the present invention result in improved activation of the bacteria, e.g. in the form of faster reconstitution and growth, advantageously the invention can allow the health benefit of the bacteria to be improved or the present invention may allow lower or less frequent doses of the selected bacteria to be used to achieve the same health benefits.

Thus, for example, bacteria which have an anti-inflammatory activity (as well as the ability to utilize citrate as an external electron acceptor) are preferred in some embodiments. *Lactobacillus reuteri* DSM 17938 would be such an example.

As described elsewhere herein the present invention finds particular use in the treatment of certain diseases or conditions in a subject.

Appropriate doses of the bacteria for use in the formulations, preparations, methods and uses of the invention as described herein can be chosen depending on the disease or condition to be treated, the mode of administration and the formulation concerned.

Thus, preferably said dosage is a therapeutically effective dosage which is appropriate for the type of mammal and condition being treated and is appropriate to give rise to the desired therapeutic effects or health benefits. For example, daily doses of $10^5$ to $10^{10}$, for example $10^6$ to $10^9$, or $10^6$ to $10^8$, or $10^8$ to $10^{10}$ total CFUs of bacteria may be used. A preferred daily dose is around $10^9$ or $10^{10}$ total CFUs, e.g. $10^9$ to $10^{10}$ total CFUs. These doses can also equate to exemplary doses per ml, where preferably a 1 ml dose is administered.

The ability of a bacterial strain to utilize citrate as an external electron acceptor (for example during fermentation of sugars) would be well understood by a person skilled in the art and could be readily determined using standard techniques. For example, one option is to test for such an ability by simply adding citrate to the growth medium and if that results in a faster, better or improved growth or growth rate of the bacteria, then it can be concluded that the bacterial strain can utilize citrate as an electron acceptor. Alternatively the utilization of citrate can be assessed by measuring whether citrate is consumed by the bacteria, for example by measuring whether citrate concentration in the growth medium is depleted when the bacteria grow.

Another option would be to screen strains of bacteria for the presence of genes encoding one or more (e.g. 2 or more, 3 or more, 4 or more, etc., or all) of the enzymes involved in the metabolism of citrate, for example in the conversion of citrate to succinate (e.g. via oxaloacetate, malate or fumarate). Thus, strains can be screened for the presence of one or more (or preferably all) of the following enzymes: EC: 1.1.1.37: malate dehydrogenase; EC: 1.2.4.1; pyruvate dehydrogenase (acetyl-transferring); FC: 1.3.99.1: succinate dehydrogenase; EC: 1.8.1.4: dihydrolipoyl dehydrogenase; EC: 2.3.1.12: dihydrolipoyllysine-residue acetyltransferase; EC: 4.1.3.6: citrate (pro-3S)-lyase (3 subunits represented by 3 different genes); EC: 4.2.1.2: fumarate hydrates. The presence of the citrate lyase enzyme is particularly important. The bacterial strains may also be screened for the presence of a citrate permease enzyme.

The use of bacteria which have the ability to utilize citrate as an external electron acceptor means that formulations and preparations of the present invention contain sources of citrate, e.g. citrate ions, for example citrate salts such as sodium citrate (e.g. trisodium citrate dihydrate), or other metal salts of citrate or citric acid. Preferred salts are those which have a minimal influence on pH, e.g. those which can be present in buffered solutions at around neutral pH, e.g. pH 6.0 to 7.5.

The present inventors have surprisingly shown that the presence of citrate in the bacterial formulations, i.e. the exposure of the bacteria to a preparation or formulation comprising citrate, results in improved (e.g. more rapid) activation of the bacteria, in particular in terms of improved reconstitution of the bacteria, e.g. from a freeze dried or lyophilized or otherwise dormant preparation, or improved growth of the bacteria, in comparison to formulations and preparations which do not contain citrate.

Thus, citrate should be in the final formulation at the time of administration to the patient (e.g. to act as an excipient) for faster activations compared to if citrate is not included. This means that one convenient way to practice the invention is to add citrate to the wet bacterial preparation or slurry just before freeze-drying or freezing or otherwise making the bacteria dormant (so it is available when the dormant bacteria is activated). An alternative convenient way to practice the invention is to add citrate as a dry ingredient to the formulation of already dry (e.g. freeze dried or lyophilised) bacteria so that citrate is again present in the final formulation and available when the dormant bacteria is activated. Alternatively the citrate can be added to or can be present in the medium or other solution used to make up the final formulation for administration to the patient (e.g. used to dissolve or reconstitute or activate the frozen, freeze dried or lyophilized or otherwise dormant bacteria).

An appropriate concentration of citrate to achieve the activation, e.g. the improved activation, of the bacteria in accordance with the present invention can be established by a person skilled in the art by any appropriate methods, for example by exposing the bacteria to citrate ions at differing concentrations and observing the effect on reconstitution and/or growth. Concentrations that for example act to stimulate improved growth (or growth rate), preferably significantly improved growth (or growth rate) of bacteria are appropriate. Exemplary concentrations are 0.01 or 0.05 mg/ml to 100 mg/ml, e.g. 0.05 or 0.1 mg/ml to 1.0, 2.0, 3.0, 5.0, 10.0, 20.0, 30.0 or 50.0 mg/ml. Alternative concentrations might be 1.0, 2.0, 3.0, 5.0, 10.0, 20.0, 30.0 or 50.0 mg/ml to 100 mg/ml. A preferred concentration might be 0.05 or 0.1 mg/ml to 5.0 or 3.0 or 2.0 or 1.0 or 0.5 mg/ml, e.g. 0.2 to 0.7 mg/ml, e.g. 0.3 to 0.6 mg/ml. These values can also be appropriate for equivalent mgs/dose given to the subject.

For example, the present inventors have shown that when citrate is present in a formulation, for example in a lyophilized or freeze dried bacterial formulation, then, in presence of citrate, the bacteria show faster or improved growth (growth rate), for example take a reduced amount of time to achieve a certain optical density (OD) when compared to the absence of citrate. Thus, preferred concentrations of citrate (citrate ions) are those that can give rise to such observations, e.g. a faster or improved growth or a faster or improved growth rate in the presence versus the absence of citrate. In particular, preferred concentrations of citrate are those that can give rise to or result in the bacterial strains achieving a certain OD or percentage rise in OD in a shorter time, preferably a significantly shorter time, than when citrate is absent. Appropriate methodology is shown in the Examples and FIG. 3. For example, conveniently one can measure the time it takes for the bacteria to achieve a 1%, 2%, 3%, 4% or 5%, or a greater than 1%, 2%, 3%, 4% or 5%, increase in OD (for example a 3% or a greater than 3% increase in OD), and observe the concentrations of citrate where this happens more quickly, preferably significantly more quickly, with citrate present versus absent (i.e. in the presence of citrate compared to the absence). Such concentrations of citrate would be appropriate for use. Any appropriate measure of bacterial growth or growth rate or bacterial numbers can be used. For example, any appropriate technique for measuring OD can be used, for example appropriate turbidity experiments as shown in the Examples.

The ability of bacteria to grow more quickly or to show an improved growth rate in the presence of citrate is also an example of the activation of bacteria in accordance with the present invention.

The live bacteria of the invention herein may be lyophilized, fresh, frozen, freeze-dried, spray-dried or the like and may be in any formulated product, including in an oil, or aqueous solution, or suspension, or emulsion or the like or an other formulation which is administered to the neonate in an enteral way, for example in a tube-feeding delivery system, via an oral route or via a rectal route.

In accordance with the present invention citrate needs to be present in the final formulation which is administered to patients.

In preferred embodiments of the invention the bacteria to be activated are dried or otherwise dormant, preferably frozen, lyophilized or freeze dried. Thus, in certain preferred embodiments the methods of the invention further comprise a step in which the bacteria are lyophilized or freeze dried or otherwise made dormant (e.g. by freezing) before the activation takes place. Preferably citrate (and optionally the carbon source or sugar, e.g. lactose) is present in such formulations or preparations of dormant bacteria (in other words the bacteria is exposed to said citrate and optionally said carbon source).

In particularly preferred embodiments, the citrate (and optionally the carbon source or sugar, e.g. lactose) is present in the freeze dried or otherwise dry or solid formulation of dormant bacteria (e.g. the citrate is present in the lyophilization medium). Preferably the citrate is added just before lyophilisation or otherwise making the bacteria dormant, for example is added to or forms a component of the lyophilization medium or freezing medium, as opposed to for example being used in the growth medium used to cultivate and expand (grow) the population of live bacteria in the steps before lyophilisation or freezing occurs (in other words the citrate is preferably not used during growth of the bacteria).

Such preparations of dry components (dry formulations) can be prepared in any appropriate way. For example, the individual components in the final product can be combined together in a liquid formulation and then lyophilized or dried, or the individual dry (or lyophilized) components, including the dry or lyophilized bacteria, can be mixed or blended together to form the dry formulation. Both of these types of dry formulation can then be reconstituted to form an appropriate citrate and live bacteria containing final solution or formulation for administration to the patients.

As set out elsewhere herein, citrate should be in the final formulation at the time of administration to the patient (e.g. to act as an excipient) for faster activations compared to if citrate is not included. This means that one convenient way to practice the invention and to expose the bacteria to citrate is to add citrate to the wet bacterial preparation or slurry just before freeze-drying or freezing (so it is available when the dormant bacteria is activated). An alternative convenient way to practice the invention is to add citrate as a dry ingredient to the formulation of already dry (e.g. freeze dried or lyophilised) bacteria so that citrate is again present in the final formulation and available when the dormant bacteria is activated. Alternatively the citrate can be added to or can be present in the medium (e.g. growth medium) or other solution used to make up the final formulation for administration to the patient (e.g. used to dissolve or reconstitute or dilute the frozen, dried or lyophilized, or otherwise dormant bacterial product).

Thus, in preferred embodiments of the invention said citrate is present in the frozen, lyophilized, freeze-dried or otherwise dormant bacterial preparation as well as in the final formulation for administration to the subject.

Where the live bacteria are lyophilized or frozen, it is a particular advantage of the invention that the presence of citrate allows improved activation of the bacteria when they are reconstituted from the dried or dormant form. Such improved activation can take the form of more rapid reconstitution or growth. In other words the presence of citrate helps kick start or improves the wake up of the bacteria from their lyophilized (dry) or otherwise dormant state.

Thus, the concept behind the present invention is for citrate to be present at or around the timepoint when the bacteria goes from a dormant (e.g. frozen or freeze dried) state to an active state, meaning that the citrate is in the final formulation which is administered to the patient (e.g. as part of the medium or buffer used to reconstitute or resuspend the dormant bacteria for administration, or in the freeze-dried or frozen or otherwise dormant preparation itself, e.g. the citrate is added just before lyophilisation or freezing of the bacteria takes place).

As described elsewhere herein, this is particularly advantageous in subjects that have minimal nutrients in the stomach or intestine to otherwise provide nutrients for the activation and growth of the bacteria. In some embodiments of the invention, some growth of the bacteria may already have occurred before the formulation reaches the intestine of the patient, e.g. during its reconstitution and administration to the patient.

Although citrate is an essential component (e.g. an excipient) in the product formulations, compositions and preparations of the invention (e.g. in the formulations to be administered into the gastrointestinal tract of patients), other components or excipients are also preferably provided.

For example, the presence of one or more appropriate carbon sources, for example which the live bacteria can use as a growth substrate, is a preferred component. Appropriate carbon sources can readily be determined depending on the nature of the live bacteria in the formulations. However, preferred carbon sources are carbohydrates such as sugars. Lactose is a preferred sugar for use. However, any other appropriate sugar can be used (for example providing that it supports the growth of the bacteria), for example sucrose, fructose, glucose or galacto-oligosaccharides (GOS).

Thus, in preferred embodiments of the invention, the carbon source or sugar, e.g. lactose (e.g. lactose monohydrate) or alternative sugar, is brought into contact with the live bacteria together with the citrate. In other words the bacteria, citrate and a carbon source are part of the same composition or formulation or preparation.

Thus, preferred preparations of the invention comprise live bacteria as defined elsewhere herein, citrate and lactose (or other appropriate sugar as described above, in particular GOS).

Other components or excipients may also be present, for example components which are useful for the stabilization or other properties of the composition or preparation, e.g. any appropriate cryoprotectants or stabilizers. Examples include one or more components selected from the group consisting of: gelatin, sodium glutamate, maltodextrin, and ascorbic acid. Mannitol is a further optional component.

In the preparations of the invention it is preferred that the components used are in a pure or substantially pure form suitable for pharmaceutical administration to mammals, preferably humans. Thus the individual components are preferably of pharmaceutical grade which can be present in a known or precise amount rather than for example being present or added as part of a mixture of unknown amounts or complex amounts of components. Thus, although the formulations of the invention may be administered after mixing or reconstitution in breast milk (or other milk based products) which may contain citrate and lactose amongst many other things, it is preferred that the product formulations for administration to patients contain appropriately pure preparations of citrate ions, e.g. in the form of citrate salts, e.g. sodium citrate as described elsewhere herein, and lactose (e.g. lactose monohydrate) or other sugars. Thus, in preferred embodiments of the invention, the formulations are reconstituted (or diluted) in water or are aqueous formulations and do not for example involve reconstitution in or presence of a milk based product such as breast milk or formula milk. Thus, preferred formulations of the invention lack milk proteins. Alternatively viewed, preferred formulations of the invention contain or are exposed to citrate which is not provided by a milk based product such as breast milk or formula milk.

The formulations also generally contain a buffer or buffer solution to allow an appropriate pH to be retained.

Preferred formulations of the invention (in particular in terms of lactose and citrate concentrations) are as described in Table B or C. Other preferred formulations would contain an alternative citrate utilizing bacteria to *Lactobacillus reuteri* DSM 17938. An alternative preferred formulation (in particular in terms of lactose and citrate concentrations) is the citrate containing formulation as described in Table 2. Again although a preferred bacteria to be used with such a formulation is *Lactobacillus reuteri* DSM 17938, in alternative embodiments other citrate utilizing bacteria as defined herein can be used. The formulation of Table 2 is particularly useful as a lyophilization medium (or lyoprotectant) for citrate utilizing bacteria, as it results in improved activation (e.g. improved growth) of the bacteria when they are reconstituted from their lyophilized form.

As mentioned above, in preferred embodiments of the invention, citrate and lactose are both present in the bacterial preparations. These components can be present at any appropriate concentration or ratio. The citrate is present at a concentration at which activation (or improved activation) of the live bacteria occurs as described elsewhere herein. Lactose (or other sugar) is generally present in an amount such that growth of the live bacteria can be supported. In preferred embodiments of the invention, the preparation comprises a citrate to lactose ratio of 1:10 or 1:50 to 1:100, 1:200, 1:300, 1:400, 1:500 or 1:600, preferably 1:40 or 1:50 or 1:60 to 1:100, 1:200, 1:300, 1:400, 1:500 or 1:600; or 1:30 to 1:100, 1:200, 1:300, 1:400, 1:500 or 1:600, preferably 1:60 to 1:600 or 1:30 to 1:300 or 1:50 to 1:70 or 1:50 to 1:60.

Thus, another object of the invention is to provide an optimal combination of a preparation comprising citrate and lactose (or other sugar), in a ratio between 1:10 to 1:600, at least 1:60 to 1:600, preferably in a ratio between 1:30 to 1:300, or at least 1:30 to 1:300 (or any other ratio as outlined herein). One example of the amount of citrate is 0.3 mg per dose of around $1\times10^{10}$ CFU live bacteria and the amount of lactose is 16.6 mg per same dose. Another example of the amount of citrate is 0.6 mg per dose of around $1\times10^9$ CFU live bacteria and the amount of lactose is 35.7 mg per same dose. One example of the amount of citrate is 1 mg per dose of around $1\times10^9$ CFU live bacteria. The citrate can be in the range of 0.01 mg to 100 mg per dose (or at other concentrations as described herein) and the amount of lactose, or other sugar, can be calculated according to the above said ratios.

Another object of the invention is to provide a preparation comprising suitable substrate components and excipients for example lactose, sucrose, fructose, glucose, GOS, 1,2 propandediol, gelatin, sodium glutamate, maltodextrin, mannitol, ascorbic acid, citrate, trisodium citrate dihydrate and a lactic acid bacteria or other suitable bacteria, the substrate components being specifically designed to further improve reconstitution and early growth of said bacteria from the lyophilized, fresh, frozen, freeze-dried, spray-died or the like state and wherein said live bacteria comprise a lactic acid bacteria that can utilize citrate as an electron acceptor.

Another object of the invention is to provide a preparation comprising for example lactose, sucrose, fructose, glucose, GOS, 1,2 propandediol, gelatin, sodium glutamate, maltodextrin, mannitol, ascorbic acid, citrate, trisodium citrate dihydrate and a live bacteria wherein said live bacteria is *Lactobacillus reuteri* DSM 17938.

Another object of the invention is to provide a preparation comprising for example lactose monohydrate, hydrolyzed gelatin, monosodium glutamate, maltodextrin, ascorbic acid, trisodium citrate dihydrate and a live bacteria wherein said live bacteria is *Lactobacillus reuteri* DSM 17938. Preferred concentrations are outlined in Examples 2 and 3. Particularly preferred concentrations of citrate are either 0.3 mg/dose or 0.6 mg/dose, or for example a range of from 0.3 to 0.6 mg/dose. Preferred concentrations of bacteria are $1\times10^9$ CFU or $1\times10^{10}$ CFU per dose, or for example a range of from $1\times10^9$ CFU to $1\times10^{10}$ CFU per dose. $1\times10^{10}$ CFU is particularly preferred, optionally in combination with a citrate concentration of 0.3 mg/dose.

Another object of the invention is to provide an optimal combination of a preparation comprising citrate and lactose, or other sugar, in a ratio between 1:10 to 1:600, at least 1:60 to 1:600.

As set out elsewhere herein the citrate activated bacteria prepared, obtained or obtainable by the methods of the present invention or the citrate containing formulations or preparations of the present invention are useful in therapy, in particular for use in the treatment of a subject with a condition which will benefit from administration of a faster activated live bacteria or a bacteria with an improved growth rate. Thus, such uses, and methods of treatment of patients in need thereof involving such uses, form yet further embodiments of the invention.

Preferred concentrations of citrate and other preferred features of the bacterial preparations to be used in such therapeutic methods and uses are set out elsewhere herein. In particular, it is important that citrate is present in the final formulation for administration to said subject. However, in addition, in some embodiments of the invention the bacteria or the bacterial preparations are frozen, lyophilized or freeze dried (or the bacteria are otherwise dormant) in which case it is preferred that said citrate is present in the frozen, lyophilized, freeze dried (or dormant) bacterial preparation. It is also a preferred embodiment that said preparations are reconstituted in water before administration to said subject.

A preferred subject for the therapeutic methods and uses of the present invention is a subject which lacks or has limited nutrients in their intestine, or is a subject in which the amount of nutrients in the intestine has been deliberately restricted, e.g. for medical reasons. Alternatively said subject is a subject which requires parenteral or intravenous nutrition (in other words requires additional or supplementary nutrition by other routes, e.g. non-oral routes, or is not receiving nutrients directly to the intestine). This situation is for example quite common in premature babies or in babies suffering from or at risk of NEC. Such subjects would generally not have sufficient nutrients in their intestine to support the activation and growth of an administered preparation of bacteria to said subject, in particular would not generally be able to support the activation and growth of an administered preparation of bacteria to such an extent that a health benefit conferred by the bacteria would be observed.

Thus, it can be seen that other preferred subjects would be neonates, or infants up to one year old, or a subject which has been born prematurely (i.e. is a premature or pre-term birth).

Other preferred subjects are subjects having NEC or at risk of developing NEC, a condition which can be common in premature babies.

Other preferred subjects are subjects which are incapable of breast feeding or oral feeding or subjects where breast feeding is not feasible as described elsewhere herein. Such a situation might arise due to health problems with either the baby or the mother, for example but not limited to preterm birth, complicated delivery, functional problems (e.g. the mother is not producing any or insufficient milk, blockage of milk ducts, mastitis), mother's illness, etc., the end result being that the subject to be treated is not able to take on sufficient nutrients through breast feeding or even other oral feeding to sustain health, or ultimately life.

The term "patient" or "subject" as used herein includes any mammal, for example humans and any livestock, domestic or laboratory animal. Specific examples include mice, rats, pigs, cats, dogs, sheep, rabbits, cows and monkey. Preferably, however, the patient or subject is a human subject.

The administration of the live bacterial strains in said methods of treatment and therapeutic uses of the invention is carried out in pharmaceutically or physiologically effective amounts, to subjects (mammals, preferably humans) in need of treatment. Thus, said methods and uses may involve the additional step of identifying a subject in need of treatment.

As will be clear from the disclosure elsewhere herein, the methods and uses of the prevent invention are suitable for prevention of diseases or conditions as well as treatment of diseases or conditions, in particular for example the prevention of NEC. Thus, prophylactic treatment is also encompassed by the invention. For this reason in the methods and uses of the present invention, treatment also includes prophylaxis or prevention where appropriate.

Such preventative (or protective) aspects can conveniently be carried out on subjects at risk for developing the diseases or conditions described herein, e.g. NEC, and can include both complete prevention and significant prevention. Significant prevention can include the scenario where severity of disease or symptoms of disease is reduced (e.g. measurably or significantly reduced) compared to the severity or symptoms which would be expected if no treatment is given.

Such reduction or alleviation of conditions, diseases or symptoms thereof (e.g. clinical symptoms or severity) can thus be measured by any appropriate assay, examples of which would be well known to a person skilled in the art. Preferably the reduction or alleviation of conditions, diseases or symptoms is significant, e.g. clinically significant or statistically significant, preferably with a probability value of $\leq 0.05$. Such reduction or alleviation of conditions, diseases or symptoms are generally determined compared to an appropriate control individual or population, for example a healthy mammal or subject (or a population thereof) or an untreated or placebo treated mammal or subject (or a population thereof), or, if appropriate, the same individual subject before treatment.

As preferred embodiments of the invention concern the treatment of patients with limited or restricted nutrients in the intestine and/or or which are having difficulty eating or feeding, a preferred form or mode of administration is direct to stomach of the subject, e.g. by mouth (orogastric) or nose (nasogastric) tube, or any other form of enteral delivery. If the subject is capable, then oral delivery is also suitable. Rectal delivery may also be used.

The citrate containing compositions of the invention or for use in the invention may be formulated or reconstituted with any appropriate solution for administration to the subject, e.g. a human. For example, the preparation may be reconstituted or formulated with water (e.g. distilled water) or other aqueous solution, some kind of formulation which mimics or replicates conditions in the intestine, e.g. simulated intestinal substrate (SIS) medium, or similar, e.g. as described in the Examples, breast milk, formula milk, or any other solution suitable for enteric administration (e.g. administration as an enteral feeding product) as described above.

Preferably and advantageously water can be used to reconstitute the formulations of the invention, in particular a citrate and sugar (e.g. lactose) containing formulation as described herein. In this regard, the finding the inventors have made that the presence of citrate (and optionally an appropriate sugar such as lactose) in dry (e.g. freeze dried or lyophilized) formulations of dormant bacteria or other formulations of dormant bacteria, can result in improved activation of the live bacteria when reconstituted, means that there is no need for a more complicated, less stable and less readily available reconstitution medium such as a milk based formulation (breast or formula milk) or other formulation for enteric administration. In other words, the ability to use water to reconstitute the preferred formulations of the invention, using the knowledge that the citrate together with lactose (or other appropriate sugar) can activate the live bacteria faster, advantageously provides a means of "standardized" activation using water without needing to rely on any other source of reagent.

Preferably any of the improvements, enhancements or increases described herein (for example the positive effects on growth, growth rate, reconstitution or activation, and indeed any other such elevated effects as mentioned elsewhere herein) are measurable increases, etc., (as appropriate), more preferably they are significant increases, preferably clinically significant or statistically significant increases, for example with a probability value of $\leq 0.05$, when compared to an appropriate control level or value or sample. For example, for the evaluation of the effects of citrate, an appropriate comparison is to a sample, preparation or subject, etc., where no citrate is present.

Preferably any of the reductions or decreases described herein (for example the reduced times to reach appropriate ODs or the reduction of doses or diseases or symptoms, and indeed any other lowered effects as mentioned elsewhere herein) are measurable reductions, more preferably they are significant reductions, preferably clinically significant or statistically significant reductions, for example with a probability value of $\leq 0.05$, when compared to an appropriate control level or value or sample. For example, for the evaluation of the effects of citrate, an appropriate comparison is to a sample, preparation or subject, etc., where no citrate is present.

The invention will be further described with reference to the following non-limiting Examples:

EXAMPLES

Example 1

Growth of *Lactobacillus reuteri* in "simulated intestine substrate"

Material and Method

The growth of *L. reuteri* DSM 17938 on different combinations of sugar and electron acceptors was evaluated in "Simulated intestinal substrate" (SIS).

TABLE A

| Simulated intestinal substrate (per liter) |
|---|
| 2 g tryptone (Oxoid) |
| 2 g yeast extract |
| 1.0 g NaCl |
| 0.5 g $K_2HPO_4$ |
| 0.5 g $KH_2PO_4$ |
| 0.1 g $MgSO_4 \times 7H_2O$ |
| 0.01 g $CaCl_2 \times 2H_2O$ |
| 5.58 g MOPS |
| 1 ml Tween 80 |
| 2.5 mg Hemin (1.0 mg/ml, 2.5 ml; solved in 0.05M NaOH) |
| 1 mg Vitamin K (vitamin $K_2$; 2 mg/ml, 0.5 ml; solved in ethanol) |
| 0.4 g Cystein-HCl |

TABLE A-continued

Simulated intestinal substrate (per liter)

0.5 g bile (porcine
0.005 g $FeSO_4 \times 7H_2O$
0.05 g $MnSO_4$
100 ng $CoCl_2 \times 6H_2O$ (100 µg/ml, 1 ml)
pH was adjusted to 6.8; Autoclaved at 121° C. for 15 min
Sterile filtered sugar and electron acceptor solutions were added before inoculation.
Final concentrations: 15 mM of each.
Sugar: Galacto-oligosaccharides (GOS) or glucose.
Electron acceptor: Citrate, 1,2 propanediol or fructose.

*Lactobacillus reuteri* cells of strain DSM 17938 were first grown over night in MRS broth (Oxoid) at 37° C. After washing in phosphate-buffered saline (PBS) the bacteria were diluted 10 × in PBS. 10 µl of bacterial suspension was thereafter inoculated to 10 ml SIS (with addition of sugar and electron acceptor), and the bacteria were cultivated for 16 h at 37° C. during anaerobic conditions and no shaking.

Cultivation of *L. reuteri* DSM 1738 in SIS with Addition of Lactose and Citrate The growth of *Lactobacillus reuteri* DSM 17938 in SIS with lactose and citrate as the sugar-electron acceptor pair is evaluated in the same way as described above for GOS and citrate as the electron acceptor. The above described substrate (SIS) is used. The *Lactobacillus reuteri* DSM 17938 is growing as efficiently on lactose-citrate as on the GOS-citrate combination (data not shown).

Example 2

Formulation of a suitable product to be used in tube-feeding a premature infant at the risk of developing NEC, using the invention herein.

The IBP-9414 powder for oral suspension is a white to off white lyophilised powder provided in a clear glass vial that contains approximately $1 \times 10^9$ CFU *L. reuteri* DSM 17938 per dose and citrate and other excipients as in the table below. It is made fresh, frozen, freeze-dried, spray-dried etc. as known in the industry.

TABLE B

| Excipient | Amount |
| --- | --- |
| Formulation per dose | |
| *L. reuteri* DSM 17938 | $1 \times 10^9$ CFU |
| Lactose monohydrate | 35.7 mg |
| Hydrolysed gelatin | 23.4 mg |
| Monosodium glutamate | 23.4 mg |
| Maltodextrin | 12.7 mg |
| Ascorbic acid | 10.7 mg |
| Trisodium citrate dihydrate | 0.6 mg |

Example 3

Formulation of a suitable product to be used in tube-feeding a premature infant at the risk of developing NEC, using the invention herein.

The IBP-9414 powder for oral suspension is a white to off white lyophilised powder provided in a clear glass vial that contains approximately $1 \times 10^{10}$ CFU *L. reuteri* DSM 17938 per dose and citrate and other excipients as in the table below. It is made fresh, frozen, freeze-dried, spray-dried etc. as known in the industry.

TABLE C

| Excipient | Amount |
| --- | --- |
| Formulation per dose | |
| *L. reuteri* DSM 17938 | $1 \times 10^{10}$ CFU |
| Lactose monohydrate | 16.6 mg |
| Hydrolysed gelatin | 10.9 mg |
| Monosodium glutamate | 10.9 mg |
| Maltodextrin | 5.9 mg |
| Ascorbic acid | 5.0 mg |
| Trisodium citrate dihydrate | 0.3 mg |

Example 4

Addition of citrate to the lyoprotectant shorten the activation time of lyophilized *Lactobacillus reuteri* DSM 17938

Methods

Cultivation:

A falcon tube with 9 ml of growth medium (see Table 1) was inoculated with *Lactobacillus reuteri* DSM 17938 from a frozen stock. The pre-culture was incubated at 37° C. for 16 hours. This was followed by a second pre-culturing step where 5 ml of the first pre-culture were added to 45 ml of fresh medium. The second pre-culture was allowed to reach an optical density (600 nm) of ≥13 (~24 hours).

A fermenter with the capacity of 1.5 liters were prepared and sterilized by autoclaving at 121° C. for 20 min. All components except glucose were added to 875 ml of dH2O and autoclaved with the fermenter. A glucose solution was made with the remaining 125 ml and autoclaved separately, and thereafter added to the fermenter. The fermenter was set to a temperature of 37° C. and pH 5.5 (controlled by addition of NaOH) with a stirring at 100 rpm. The fermenter was allowed to run overnight to determine possible contaminations. Following this, 50 ml of the second pre-culture was injected and the fermenter was run for 15 hours, reaching a final optical density of 14.3.

The culture was pumped from the fermenter to a sterilized flask (took ~2.5 hours), divided into two parts that were centrifuged at 3200 rpm for 10 min. The two pellets (13.4 and 15.2 g) were washed with sodium glutamate buffer (45.2 g sodium glutamate in 1.8 liter of dH2O, filtered through a 0.2 µm sterile filter) followed by suspension in equal amounts (13.4 and 15.2 ml) of sodium glutamate buffer. The bacterial suspensions were further mixed with an equal volume of lyophilization buffer with (C) or without (N) addition of citrate (see Table 2).

TABLE 1

Composition of growth medium

| Component | Quantity (g) |
| --- | --- |
| Distilled water | 1000 ml |
| Yeast extract | 14 |
| Soy peptone | 20 |
| Di-ammonium hydrogen citrate | 5.2 |
| Sodium acetate trihydrate | 4.8 |
| Dipotassium hydrogen phosphate | 2.0 |
| Magnesium sulphate, heptahydrate | 0.1 |
| Manganese sulphate, monohydrate | 0.018 |
| Zinc sulphate, heptahydrate | 0.01 |
| Tween 80 | 0.52 |
| D-Glucose anhydrate | 54.5 |

TABLE 2

Composition of lyophilization medium

| Component | N, without citrate | C, with citrate |
|---|---|---|
| | Concentration (g/L) | |
| Lactose | 142.7 | 142.7 |
| Maltodextrin | 50.9 | 50.9 |
| Ascorbic acid | 42.7 | 42.7 |
| Gelatine | 93.6 | 93.6 |
| Monosodium glutamate* | 93.6 | 81.1 |
| Trisodium citrate dihydrate | | 2.38 |
| pH | 6.0, adjusted with sodium hydroxide | |

*The reason for a difference in sodium glutamate concentration is to adjust pH, sodium concentration and ion strength.

Lyophilization:

Prior to lyophilization the bacterial suspensions were aliquoted in volumes of 1 ml into 5 ml freeze-drying vials with rubber stoppers. The following lyophilization program was run:

TABLE 3

Lyophilization program

| Step | Temperature (° C.) | Time (h) | Pressure (µbar) |
|---|---|---|---|
| Freezing | −50 | 11 | No vacuum |
| Primary drying | −50 to −35 | 36 | 100 to 50 |
| Secondary drying | 25 | 27 | 20 |

After the completion of the second drying step, the vials were sealed without vacuum in the presence of nitrogen gas.

Quantification:

Samples for quantification of bacteria were taken from the culture before the distribution into two parts. To determine the survival rate, these results were later compared with analyses of lyophilized samples.

DNA Preparation of Fermenter Culture:

DNeasy® Blood & Tissue Handbook (cat. no. 69504) (according to protocol: Pretreatment for Gram-Positive Bacteria, with slight modifications)

Cells from the fermenter culture (1 ml) were harvested by centrifugation for 10 min at 5000 × g (7500 rpm). The supernatant was discarded and the bacterial pellet was resuspended in 180 µl enzymatic lysis buffer and incubated for 60 min at 37° C. This was followed by a bead beating step using 0.25 ml of 0.1 mm Zirconia/silica beads (Bio-Spec: Cat. No. 11079101z) in a 2 ml Micro tube PP (Sarstedt: Order no. 72.694.006) at speed 5.0 for 3×45 s (FastPrep®—24 Instrument, MP Biomedicals). The bead beating samples were incubated for 30 min at 56° C. The rest of the steps were performed according to the protocol.

PCR:

```
Primers:
DSM17f2
(TACGGGGAACGAGTTATTGC)
and

DSM17r2
(GGACGGCTTAACAAAACAGC);
Product size 216 bp
```

DreamTaq Green PCR Mastermix (2× Thermo Scientific, article number K1081) was used for the PCR reactions. PCR reactions according to this:

| Mastermix with primers | Volume per reaction |
|---|---|
| Water (PCR quality) | 3.0 µl |
| Primer, forw. (10 pmol/µl) | 1.0 µl |
| Primer, rev. (10 pmol/µl) | 1.0 µl |
| BSA (final conc. 0.1 µg/µl) | 2.5 µl |
| DreamTaq | 12.5 µl |

20 µl of Mastermix was mixed with 5 µl DNA sample and the following program was run: 98° C. 5 min//2× (95° C. 30s, 68° C. 30s, 72° C. 20s)//2× (95° C. 30s, 66° C. 30s, 72° C. 20s)//2× (95° C. 30s, 64° C. 30s, 72° C. 20s)//2× (95° C. 30s, 62° C. 30s, 72° C. 20s)//35× (95° C. 30s, 62° C. 30s, 72° C. 20s)//72° C. 5 min//16° C.

Evaluation of Activation Time:

The activation time in simulated intestinal medium (STMmod 3, see Table 4) of the two variants of lyophilized DSM 17938 (C and N) were analyzed using a computer-controlled incubator/reader/shaker (BioScreen C MBR) that measure the change in turbidity over time. The medium STMmod 3 was used to mimic the conditions in the intestine.

To each well 200 µl of STMmod 3 was added. Thereafter different volumes (100, 60, 40, 30, 25 µl) of bacterial suspension (vials with lyophilized bacteria suspended in 1 ml dH$_2$O) were added. Volumes were adjusted to 300 µl with dH2O. The analysis of each inoculation volume was done in triplicates. The BioScreen analysis was run at 37° C. for 24 hours with a 15 min interval between measurements (OD 600 nm), with the addition of a 10 s shaking step before each measuring point.

TABLE 4

Composition of simulated intestinal medium (STMmod 3)

| Component | Quantity |
|---|---|
| Distilled water | 1000 ml |
| Yeast extract | 2.0 g |
| Tryptone (oxoid) | 2.0 g |
| NaCl | 1.0 g |
| K$_2$HPO$_4$ | 0.5 g |
| KH$_2$PO$_4$ | 0.5 g |
| MgSO$_4$ × 7H$_2$O | 0.1 g |
| CaCl$_2$ × 2H$_2$O | 0.01 g |
| Tween 80 | 1 ml |
| Hemin | 2.5 mg |
| Vitamin K | 1.0 mg |
| Cystein-HCl | 0.4 g |
| Bile (porcine) | 0.5 g |
| FeSO$_4$ × 7H$_2$O | 0.005 g |
| MnSO$_4$ | 0.05 g |
| CoCl$_2$ × 6H$_2$O | 100 µg |
| pH | 6.8 |

Results

Figure 2:
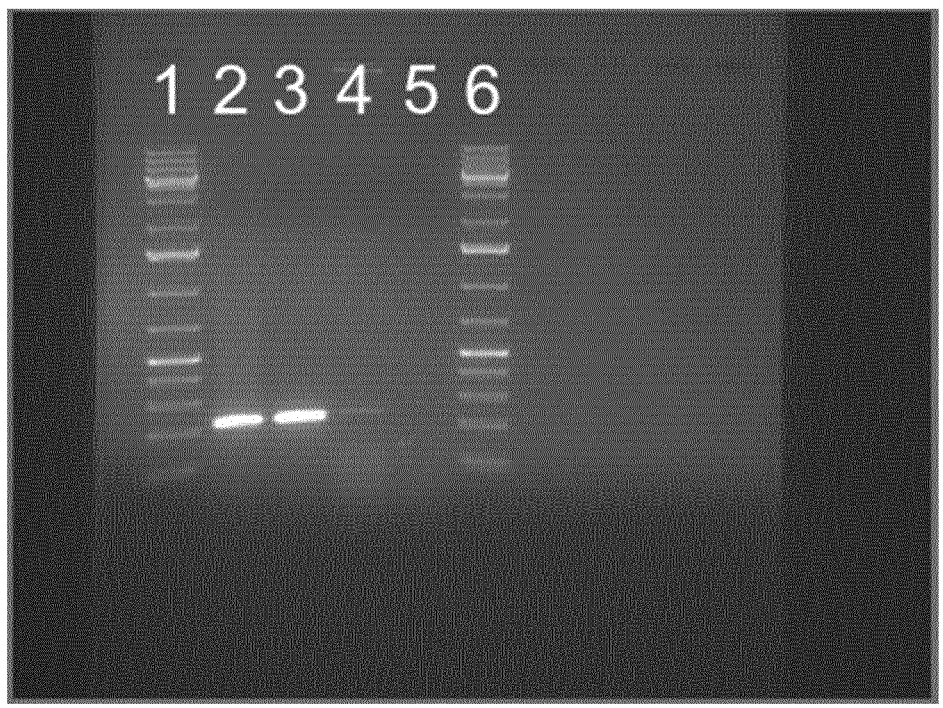
FIG. 2 shows the results from gel electrophoresis identifying the fermenter culture as DSM 17938:1. Marker (GeneRuler 1 kb Plus DNA ladder); 2. Fermenter sample 1 (66 ng/µl); 3. Fermenter sample 2 (6.6 ng/µl); 4. Positive control (bacterial suspension of DSM 17938); 5. Negative control (H2O); 6. Marker

PCR:

A PCR with the DSM 17938-specific primers were run on the DNA extractions on the fermenter culture, to confirm that the correct bacteria had been cultivated. The results indeed show that DSM 17938 was cultivated in the fermenter (FIG. 2).

Quantification:

The survival rate of DSM 17938 after the lyophilization was determined to be approximately 13% for the bacteria lyophilized with citrate (C) and 12% for the bacteria lyophilized without citrate (N) (see Table 5).

TABLE 5

Quantification, survival rate and optical density of fermenter and freeze dried cultures of DSM 17938.

| Sample | CFU/ml | Survival rate | OD (600 nm) |
|---|---|---|---|
| Fermenter culture (15 h) | $6.14 \cdot 10^9$ (±0.41) | | 14.3 |
| Lyophilized bacteria N | $6.83 \cdot 10^9$ (±3.67) | 12% | 66.3 ± 5.0 |
| Lyophilized bacteria C | $7.25 \cdot 10^9$ (±1.44) | 13% | 75.7 ± 2.1 |

Figure 3:
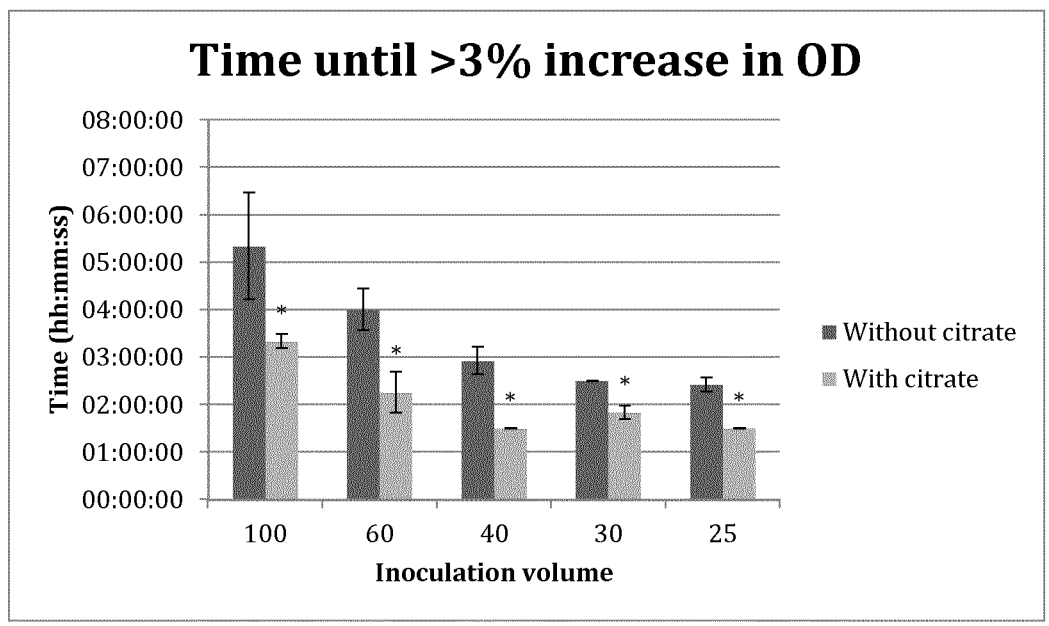
FIG. 3 shows the results from the turbidity experiments, revealing that a lyophilisation medium containing citrate causes DSM 17938 to reach an OD-increase of 3% faster compared to lyophilisation medium without citrate. *=significant difference (Student's t-test, $\alpha=0.05$).

Evaluation of Activation Time:

The results from the turbidity experiment revealed that freeze dried cultures of DSM 17938 reached a 3% increase in OD in shorter time when the lyoprotectant contained citrate (see FIG. 3).

To summarize: the results revealed that the addition of citrate (used by *L. reuteri* as an electron acceptor) in the product formulation, shorten the activation time of *Lactobacillus reuteri* DSM 17938 in simulated intestinal medium.

The invention claimed is:

1. A method of treating a neonate, a premature infant, or an infant having a condition benefiting from the administration of reconstituted live *Lactobacillus reuteri* with faster activation following dormancy, the method comprising:
   administering to the neonate, premature infant, or infant a composition comprising a therapeutically effective amount of the reconstituted live *L. reuteri* in the presence of citrate, wherein the reconstituted live *L. reuteri* use the citrate as an electron acceptor and the reconstituted live *L. reuteri* are prepared from frozen or lyophilized *L. reuteri* activated by the citrate to result in metabolizing *L. reuteri*, wherein the citrate is an external electron acceptor, and wherein the citrate is present when the *L. reuteri* is frozen or lyophilized or the citrate is added to the frozen or lyophilized *L. reuteri* prior to or during reconstitution,
   wherein the reconstituted live *L. reuteri* in the presence of citrate have a faster activation rate following dormancy compared to the activation rate following dormancy for the same *L. reuteri* that are reconstituted in the absence of citrate and the faster activation rate is a faster increase in growth over the same time period, thereby treating the condition of the neonate, premature infant, or infant that benefits from the administration of the reconstituted live *L. reuteri* with faster activation following dormancy.

2. The method of claim 1, wherein the citrate is in the form of a composition comprising a sugar.

3. The method of claim 2, wherein said sugar is lactose.

4. The method of claim 3, wherein the composition comprises a citrate to lactose ratio of 1:10 to 1:600 by weight.

5. The method of claim 1, wherein the concentration of the citrate is about 0.01 mg/ml to 10 mg/ml.

6. The method of claim 1, wherein the concentration of the citrate is about 0.01 mg/ml to 2 mg/ml.

7. The method of claim 1, wherein the reconstituted live *L. reuteri* is reconstituted live *Lactobacillus reuteri* DSM 17938.

8. The method of claim 1, wherein the increase in growth for the reconstituted live *L. reuteri* in the presence of citrate is an increase in growth of 1% or greater than 1% compared to the growth of the same *L. reuteri* that are reconstituted in the absence of citrate when measured over the same time period.

9. The method of claim 1, wherein the increase in growth for the reconstituted live *L. reuteri* in the presence of citrate is an increase in growth of 1% to about 5% compared to the growth of the same *L. reuteri* that are reconstituted in the absence of citrate when measured over the same time period.

10. The method of claim 1, wherein the condition benefiting from the administration of the composition comprising the reconstituted live *L. reuteri* and citrate is a condition in which the neonate, premature infant, or infant has difficulty feeding orally, is incapable of breast feeding or oral feeding, and/or requires additional or supplementary nutrition by parenteral or intravenous routes, and/or nutrition of the neonate, premature infant, or infant is deliberately restricted for medical reasons.

11. The method of claim 10, wherein the condition in which the neonate, premature infant, or infant has difficulty feeding orally, is incapable of breast feeding or oral feeding, and/or requires additional or supplementary nutrition by parenteral or intravenous routes, and/or nutrition of the neonate, premature infant, or infant is deliberately restricted for medical reasons is necrotizing enterocolitis (NEC) or the risk of developing NEC.

12. The method of claim 1, wherein the increase in growth is determined by measuring cell number.

13. The method of claim 12, wherein the measuring of cell number is by optical density.

14. The method of claim 13, wherein the optical density is measured at 600 nm.

15. The method of claim 1, wherein the frozen or lyophilized *L. reuteri* are frozen or lyophilized *L. reuteri* that are frozen or lyophilized, respectively, in the presence of citrate.

16. The method of claim 15, wherein the frozen or lyophilized *L reuteri* are reconstituted in an aqueous composition comprising citrate.

17. The method of claim 1, wherein the frozen or lyophilized *L. reuteri* are frozen *L. reuteri* that are frozen in the presence of citrate.

18. The method of claim 1, wherein the frozen or lyophilized *L. reuteri* are lyophilized *L. reuteri* that are lyophilized in the presence of citrate.

19. The method of claim 1, wherein the composition comprises an external electron acceptor for *L. reuteri* that consists of citrate.

* * * * *

UNITED STATES PATENT AND TRADEMARK OFFICE
CERTIFICATE OF CORRECTION

| | | |
|---|---|---|
| PATENT NO. | : 12,171,793 B2 | Page 1 of 1 |
| APPLICATION NO. | : 15/320996 | |
| DATED | : December 24, 2024 | |
| INVENTOR(S) | : Stromberg et al. | |

It is certified that error appears in the above-identified patent and that said Letters Patent is hereby corrected as shown below:

In the Specification

Column 19, Line 59: Please correct "(TACGGGGAACGAGTTATTGC)" to read --(TACGGGGAACGAGTTATTGC; SEQ ID NO: 1)--

Column 19, Line 62: Please correct "(GGACGGCTTAACAAAACAGC)" to read --(GGACGGCTTAACAAAACAGC; SEQ ID NO: 2)--

Signed and Sealed this
First Day of July, 2025

Coke Morgan Stewart
*Acting Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tacggggaac gagttattgc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ggacggctta acaaaacagc                                              20
```